(12) United States Patent
Hoedl et al.

(10) Patent No.: US 10,646,724 B2
(45) Date of Patent: May 12, 2020

(54) BRACHYTHERAPY DEVICES AND RELATED METHODS HAVING MICROENCAPSULATED BRACHYTHERAPY MATERIALS

(71) Applicant: Civatech Oncology, Research Triangle Park, NC (US)

(72) Inventors: Seth A. Hoedl, Somerville, MA (US); Bruce Kitzman, Durham, NC (US)

(73) Assignee: Civatech Oncology, Research Triangle Park, NC (US)

(*) Notice: Subject to any disclaimer, the term of this patent is extended or adjusted under 35 U.S.C. 154(b) by 0 days.

(21) Appl. No.: 15/657,898

(22) Filed: Jul. 24, 2017

(65) Prior Publication Data
US 2019/0038915 A1 Feb. 7, 2019

Related U.S. Application Data

(63) Continuation of application No. 13/594,214, filed on Aug. 24, 2012, now abandoned.

(60) Provisional application No. 61/527,391, filed on Aug. 25, 2011.

(51) Int. Cl.
*A61N 5/10* (2006.01)

(52) U.S. Cl.
CPC .... *A61N 5/1001* (2013.01); *A61N 2005/1023* (2013.01); *A61N 2005/1024* (2013.01)

(58) Field of Classification Search
CPC .. A61N 5/1001; A61N 5/1002; A61N 5/1007; A61N 5/1014; A61N 5/1015; A61N 5/1027; A61N 2005/1019; A61N 2005/1023; A61N 2005/1024
See application file for complete search history.

(56) References Cited

U.S. PATENT DOCUMENTS

| | | | | |
|---|---|---|---|---|
| 2002/0055667 | A1* | 5/2002 | Mavity | A61N 5/1027 600/3 |
| 2004/0153138 | A1* | 8/2004 | Murphy | A61B 17/12022 623/1.15 |
| 2008/0058919 | A1* | 3/2008 | Kramer-Brown | A61L 31/08 623/1.34 |
| 2011/0118532 | A1* | 5/2011 | Kaplan | A61K 41/0038 600/8 |

* cited by examiner

*Primary Examiner* — Thaddeus B Cox
(74) *Attorney, Agent, or Firm* — Myers Bigel, P.A.

(57) ABSTRACT

A brachytherapy device includes a bioabsorbable support and a plurality of microcapsules on the support. Each of the plurality of the microcapsules includes a plurality of microspheres and a bioabsorbable microcapsule wall that encloses the plurality of microspheres. The plurality of microspheres includes radiation-emitting microspheres comprising a radioactive material, radio-opaque microspheres comprising a radio-opaque material or a combination thereof.

18 Claims, 4 Drawing Sheets

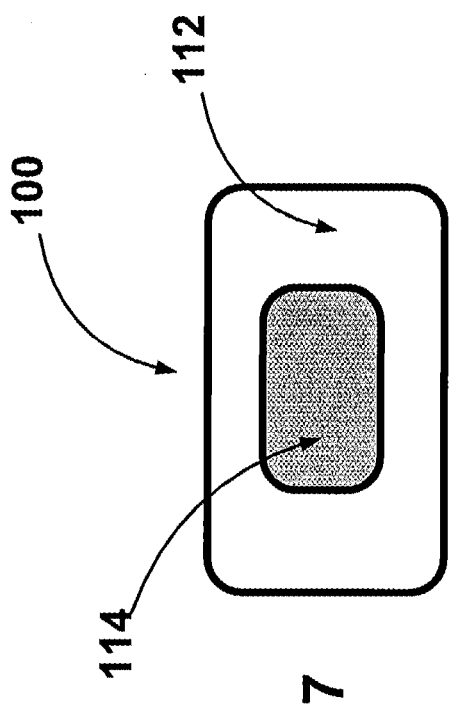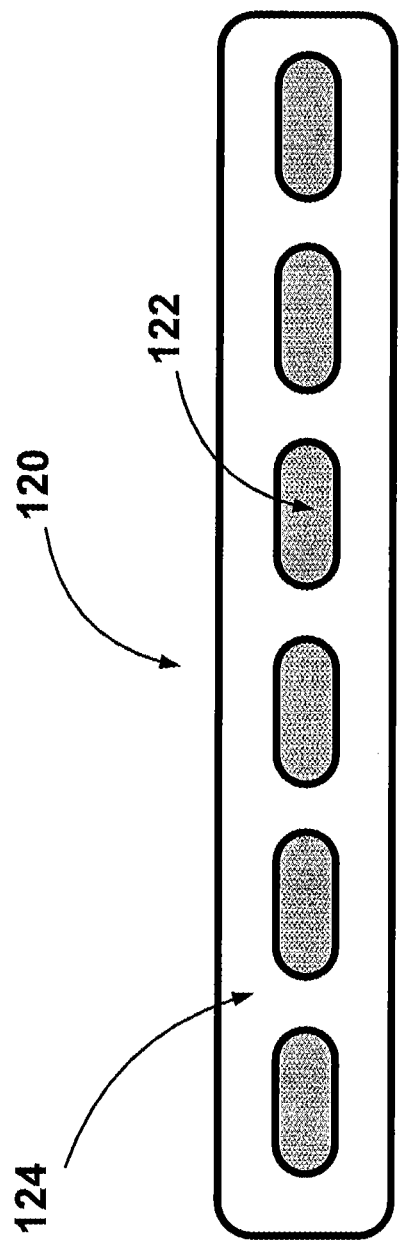

BRACHYTHERAPY DEVICES AND RELATED METHODS HAVING MICROENCAPSULATED BRACHYTHERAPY MATERIALS

RELATED APPLICATIONS

This application is a continuation of U.S. patent application Ser. No. 13/594,214 filed Aug. 24, 2012, which claims priority to U.S. Provisional Application Ser. No. 61/527,391, filed Aug. 25, 2011, the disclosure of which is hereby incorporated by reference in its entirety.

FIELD OF THE INVENTION

The present invention relates to brachytherapy, and more particularly, to brachytherapy devices having microencapsulated radioactive materials.

BACKGROUND

Low-dose rate brachytherapy may provide a viable alternative to external beam radiation and high-dose rate brachytherapy. Although low-dose brachytherapy is most often used for prostate cancer, low-dose brachytherapy is being considered increasingly with respect to other cancers, such as breast cancer.

Although there are encouraging results to suggest that low-dose rate brachytherapy seeds currently used in prostate cancer can eradicate early stage breast cancer, because these seeds were designed to treat prostate instead of breast cancer, there are several clinical issues that may prohibit broad adoption. For example, some medical physicists have expressed concern that the radiation dose delivered to the tissue will be uncertain due to changes in the lumpectomy cavity and seed migration. In addition, there is a great concern that radio-opaque markers in the seeds, used to identify the location of the seeds in post-implant CT scans, will confuse subsequent mammograms by either looking like a local recurrence or hiding a local recurrence in the "shadow" of the radio-opaque marker. In addition, some women may prefer to not have permanent, metal implants in a breast.

SUMMARY OF EMBODIMENTS OF THE INVENTION

In some embodiments, a brachytherapy device includes a bioabsorbable support and a plurality of microcapsules on the support. Each of the plurality of microcapsules includes a plurality of microspheres and a bioabsorbable microcapsule wall that encloses the plurality of microspheres. The plurality of microspheres includes radiation-emitting microspheres comprising a radioactive material, radio-opaque microspheres comprising a radio-opaque material or a combination thereof.

In some embodiments, the plurality of microspheres have a diameter of about 1 to 20 microns. The plurality of microspheres may be sized and configured so as to be subject to phagocytosis by macrophages in a subject after bioabsorption of the bioabsorbable support and the bioabsorbable microcapsule wall. In some embodiments, the bioabsorbable support and the microcapsule wall have a decay time that is greater than about two and a half times a half life of the radioactive material. Some of the plurality of microspheres may/include a radioactive core and an outer wall. The radioactive core may include a radioactive material and a biocompatible polymer and/or ceramic. The radioactive core may include a porous material and a radio-isotope deposited therein. The outer wall may include glass or acrylic.

In some embodiments, the microcapsule wall includes a poly-lactide, poly-glycolide, polycaprolactone, poly-trimethylene-carbonate, polyanhdride, co-polymers formed thereof, and/or combinations thereof.

In some embodiments, the bioabsorbable support includes a poly-lactide, poly-glycolide, polycaprolactone, poly-trimethylene-carbonate, polyanhdride, co-polymers formed thereof, and/or combinations thereof.

In some embodiments, the bioabsorbable support is configured to seal the microcapsules therein after implantation.

In some embodiments, a size and/or thickness of the bioabsorbable support and/or microcapsule walls is configured to release the microspheres after a predetermined time. The predetermined time may be greater than two and a half times a half life of the radioactive material. The predetermined time may be about three months.

In some embodiments, the bioabsorbable support comprises a seed casing that is configured to seal the plurality of microcapsules therein prior to bioabsorption of the support.

In some embodiments, the bioabsorbable support comprises a substantially linear support having a plurality of wells therein that is configured to seal the plurality of microcapsules in respective ones of the plurality of wells prior to bioabsorption of the support.

In some embodiments, the bioabsorbable support comprises a substantially planar support that is configured to seal the plurality of microcapsules therein prior to bioabsorption of the support.

In some embodiments, a microcapsule includes a microcapsule outer wall, and a plurality of microspheres enclosed by the microcapsule outer wall, wherein the plurality of microspheres comprises radiation-emitting microspheres comprising a radioactive material, radio-opaque microspheres comprising a radio-opaque material or a combination thereof.

In some embodiments, the plurality of microspheres have a diameter of about 1 to 20 microns. The plurality of microspheres may be sized and configured so as to be subject to phagocytosis by macrophages in a subject after bioabsorption of the bioabsorbable support and the bioabsorbable microcapsule wall.

In some embodiments, some of the plurality of microspheres comprises a radioactive core and an outer wall. The radioactive core may include a radioactive material and a biocompatible polymer and/or ceramic. The radioactive core may include a porous material and a radio-isotope deposited therein. The outer wall may include glass or acrylic. The microcapsule wall may include a poly-lactide, poly-glycolide, polycaprolactone, poly-trimethylene-carbonate, polyanhdride, co-polymers formed thereof, and/or combinations thereof.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 7 is a cross-sectional schematic diagram of a brachytherapy seed having a radioactive core comprising microcapsules according to some embodiments of the present invention.

FIG. 8 is a cross-sectional schematic diagram of a generally linear brachytherapy device having a radioactive core comprising microcapsules according to some embodiments of the present invention.

DETAILED DESCRIPTION OF EMBODIMENTS OF THE INVENTION

Figure 1:
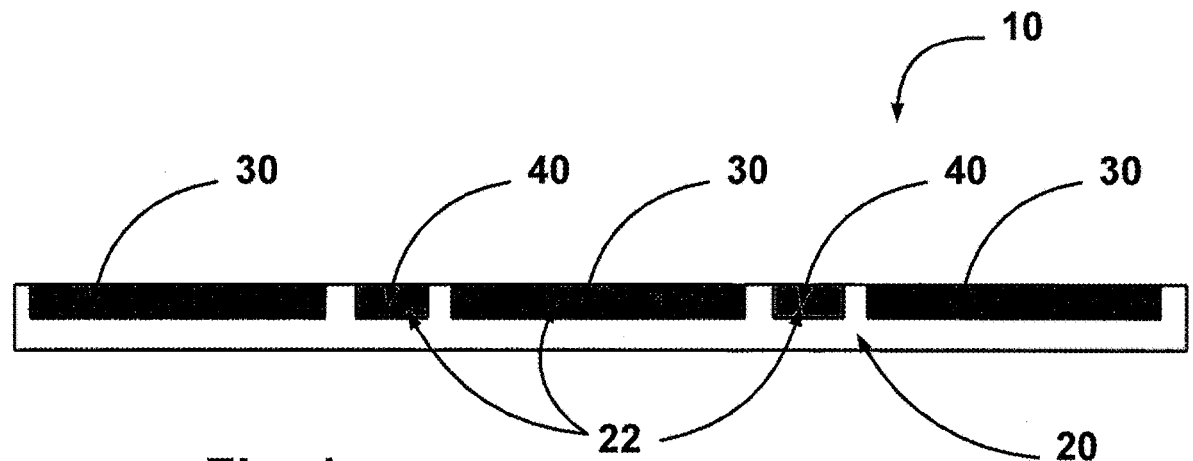
FIG. 1 is a cross-sectional schematic diagram of a low-dose-rate (LDR) brachytherapy device according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

"Biocompatible" as used herein refers to a material and any metabolites or degradation products thereof that are generally non-toxic to the recipient and do not cause any significant adverse effects to the subject. The criteria for defining significant adverse effects may be based on criteria used by regulatory agencies such as the U.S. Food and Drug Administration.

"Biodegradable" or "bioabsorbable" refers to a material that will degrade or erode under physiologic conditions to smaller units or chemical species that are capable of being metabolized, eliminated, absorbed or excreted by the subject.

Although embodiments are described herein as relating to breast cancer and implantation in breast tissue, it should be understood that other types of cancer may be treated using the methods and devices described herein, including lung cancer, bladder cancer, colon cancer, kidney or renal cancer, pancreatic cancer, prostate cancer thyroid cancer, head and neck cancers and soft tissue sarcomas.

Embodiments according to the present invention will now be described with respect to FIGS. 1-10.

Figures 2, 3:
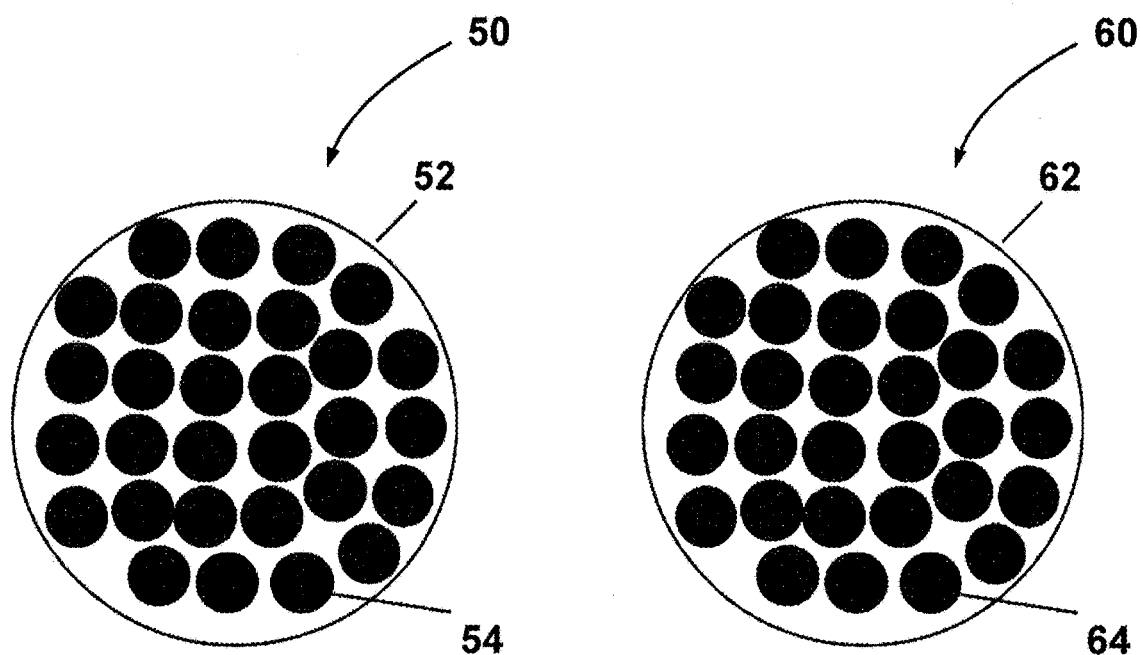
FIG. 2 is a cross-sectional schematic diagram of a bioabsorbable microcapsule including radioactive microspheres according to some embodiments of the present invention.
FIG. 3 is a cross-sectional schematic diagram of a bioabsorbable microcapsule including radio-opaque microspheres according to some embodiments of the present invention.
Figure 4:
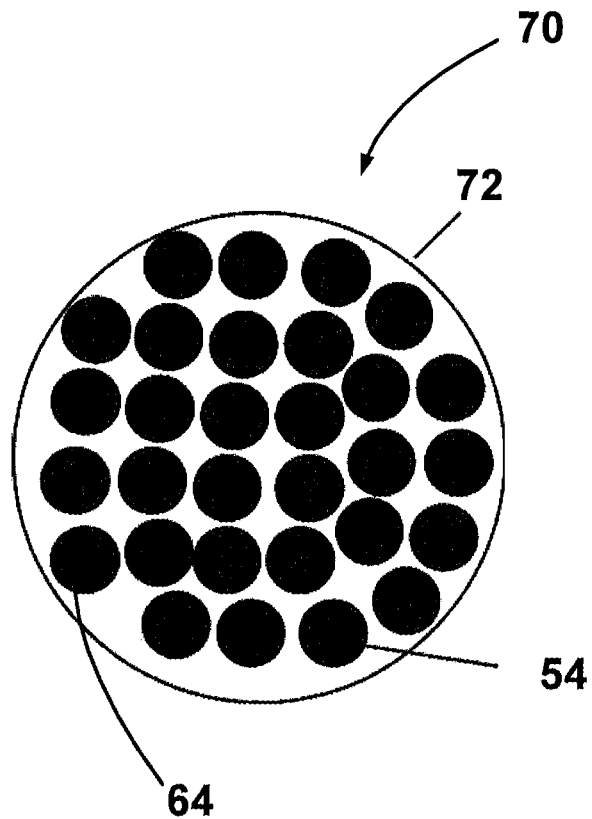
FIG. 4 is a cross-sectional schematic diagram of a bioabsorbable microcapsule including radioactive microspheres and radio-opaque microspheres according to some embodiments of the present invention.

An exemplary device 10 in which a substrate or scaffold support 20 includes a plurality of wells 22 is shown in FIG. 1. The wells 22 may include either a radioactive material 30 or a radio-opaque marker material 40 or a combination thereof. As illustrated in FIGS. 2-3, the radioactive material 30 may be provided by a plurality of radiation treatment microcapsules 50 (FIG. 2) and the radio-opaque marker material 40 may be provided by a plurality of radio-opaque microspheres 50 (FIG. 3). The radiation treatment microcapsules 50 include a bioabsorbable microcapsule body or wall 52 that has radioactive microspheres 54 embedded therein. The radio-opaque microcapsules 60 include a bioabsorbable microcapsule body or wall 62 that has radio-opaque microspheres 64 embedded therein. Although the device 10 of FIG. 1 is illustrated with respect to wells 22 that include either a radioactive material 30 or a radio-opaque marker material 40, it should be understood that the wells 22 may include both radiation treatment microcapsules 50 and radio-opaque microcapsules 60. Moreover, as illustrated in FIG. 4, a microcapsule 70 is shown that includes both radioactive microspheres 54 and radio-opaque microspheres 64. Therefore, microcapsules according to some embodiments may include either radioactive or radio-opaque microspheres or a combination thereof.

Figure 5:
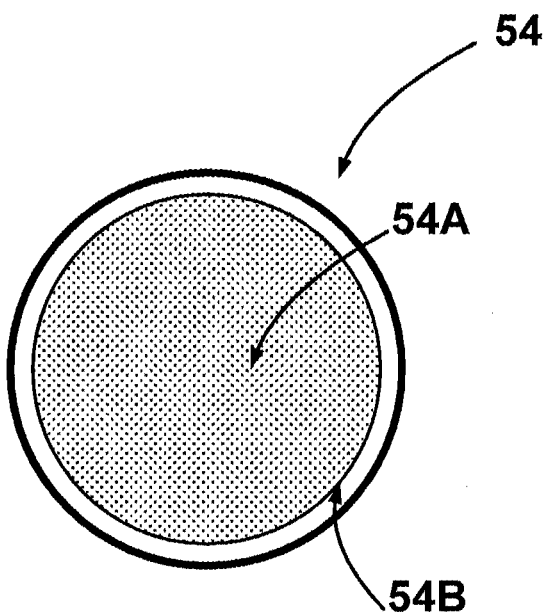
FIG. 5 is a cross-sectional schematic diagram of a radioactive microsphere according to some embodiments of the present invention.
Figure 6:
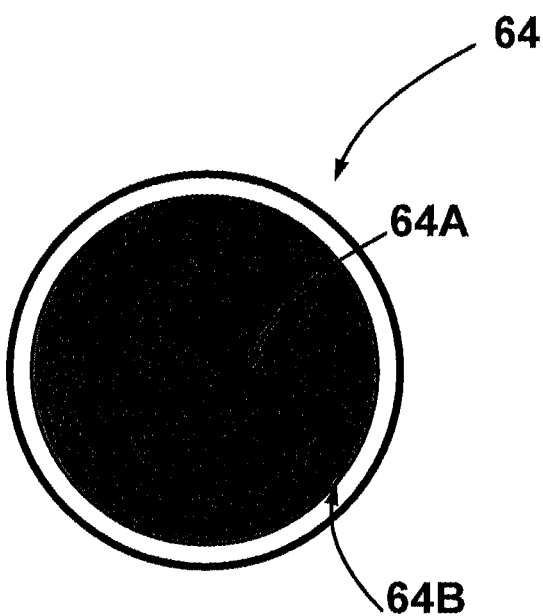
FIG. 6 is a cross-sectional schematic diagram of a radio-opaque microsphere according to some embodiments of the present invention.

In this configuration, LDR brachy therapy devices according to some embodiments may addresses concerns such as future imaging (e.g., mammography) and cosmetic concerns of LDR brachytherapy, including the potential toxicity of the radio-isotope or its decay products to healthy tissue as they are released from the bioabsorbable device. The microcapsules 50, 60, 70 (FIGS. 2-4) and various components of the support 20 (FIG. 1) may be biocompatible and biodegradable and/or bioabsorbable; however, the radioactive microspheres 54 and radio-opaque microspheres 64 may be biocompatible, but not biodegradable or bioabsorbable. Thus, the biodegradable/bioabsorbable components of the device 10 may be selected such that they degrade or absorb into the body after a substantial amount of radioactive decay has occurred. After the biodegradable components degrade/absorb into the body, the microspheres 54, 64 disperse within the body. In some embodiments, the radioactive microspheres 54 and the biodegradable components of the device 10 may be selected so that the time that the biodegradable/bioabsorbable components take to degrade and release the radioactive microspheres 54 is sufficient to allow significant decay of the radioactive material in the microspheres 54. Stated otherwise, the biodegradable components of the device 10 permit the radioactive microspheres 54 to be fixed in a desired location during radiation treatment, but once the radioactive material has decayed such that its therapeutic value is decreased and its potential to deliver radiation to healthy tissue is reduced, the biodegradable components of the device 10 degrade and/or are absorbed into the body and the microspheres 54, 64 are released. In some embodiments, devices described herein will not directly expose a patient to the radioactive components after it is bioabsorbed or biodegraded. As illustrated in FIGS. 5-6, the microspheres 54, 64 may include a respective microsphere core 54A, 64A and an outer microsphere wall 54B, 64B. The walls 54B, 64B may be biocompatible and may provide a barrier between the respective cores 54A, 64A and tissue in the body.

In some embodiments, the size of the microspheres 54, 64 is selected so that macrophages in the patient's body can engulf the microspheres in the process of phagocytosis.

Although embodiments according to the present invention are described with respect to the linear or string-shaped device 10 of FIG. 1, it should be understood that the microcapsules according to some embodiments may be provided as part of LDR brachytherapy devices having any suitable shape and configuration, including conventional brachytherapy seed shapes, planar sheets, uni-directional devices having a radiation shielding material and the like. Examples of LDR brachytherapy devices that may be suitable for use with the microcapsules described herein, for example, with respect to FIGS. 2-4 may be found, e.g., in U.S. Pat. No. 7,686,756 and U.S. Publication No. 20090275793, the disclosures of which are hereby incorporated by reference in their entirety. For example, as shown in FIG. 7, a brachytherapy device 110 according to embodiments of the present invention includes a sealed housing or casing 112 and a radioactive material 114. The radioactive material 114 may include one or more of the microcapsules 50, 60, 70. The sealed casing 112 may be a biocompatible and/or bioabsorbable material. According to some embodiments, the type of bioabsorbable material in the casing 112 may be evaluated to ensure that the radioactive material 114 is sealed for a sufficient period of time, such as until the radioactive material 114 decays to a safe level, such as less than 10%, less than 5% or even less than 1% of the original radioactivity.

Figure 9:
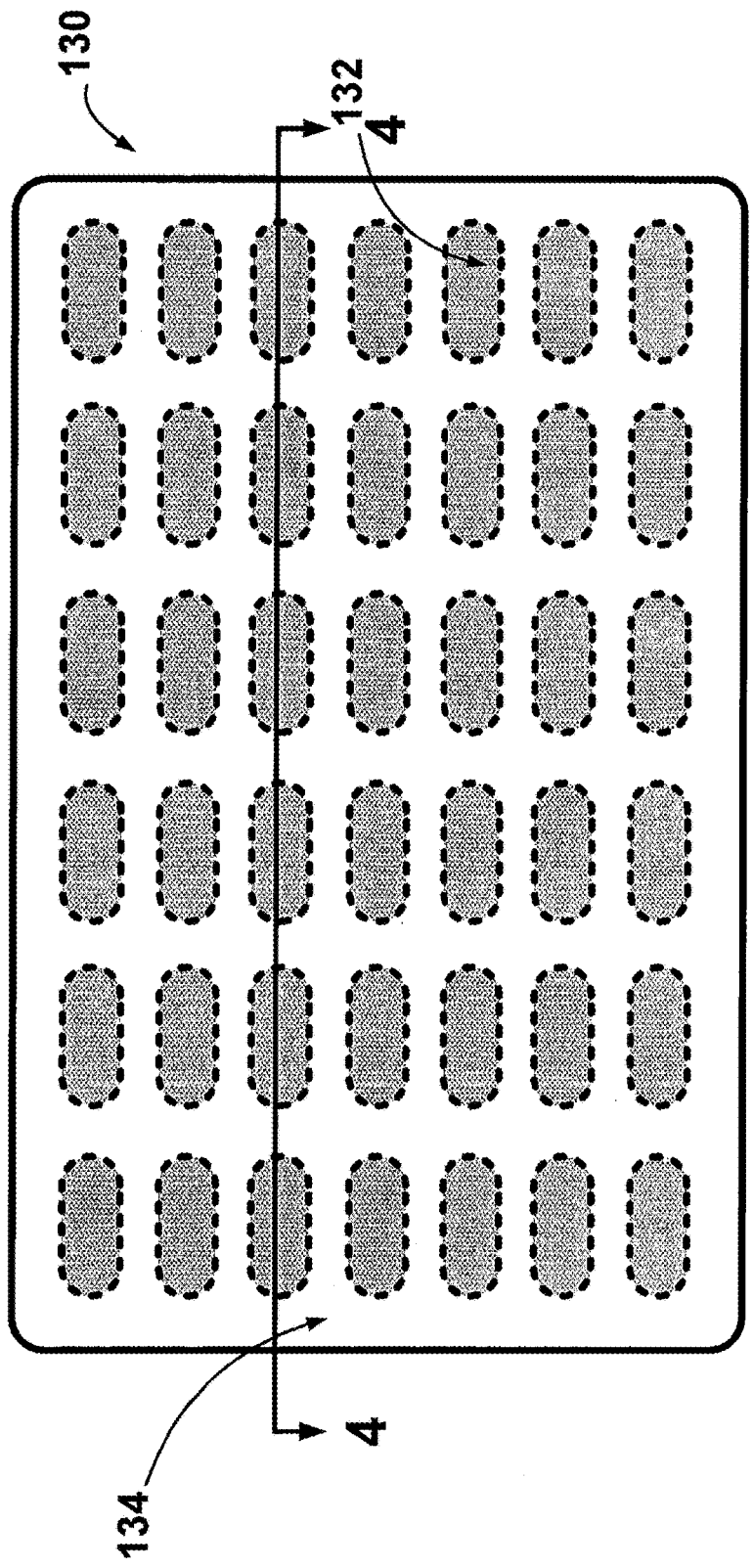
FIG. 9 is a top view schematic diagram of a generally planar brachytherapy device having a radioactive core comprising microcapsules according to some embodiments of the present invention.
Figure 10:
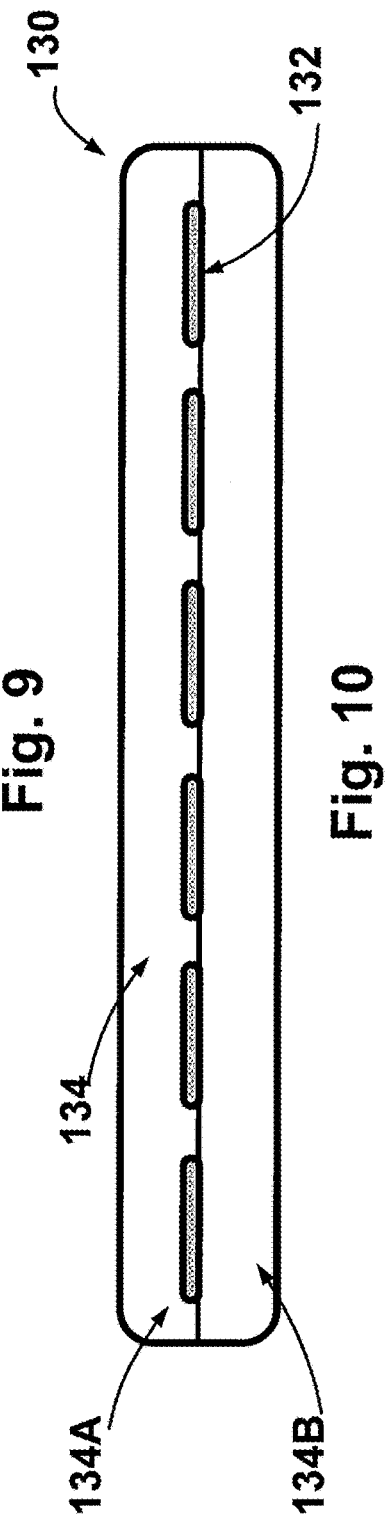
FIG. 10 is a cross-sectional side view of the brachytherapy device of FIG. 9.

Although the device 110 is illustrated as a "point source" or "seed" shape, any suitable shape of device or encapsulation of the radioactive material may be used. For example, as shown in FIG. 8, a device 120 includes a plurality of globules of radioactive material 122 encapsulated in a sealed casing 124. The radioactive material 122 may include one or more of the microcapsules 50, 60, 70. The linear device 20 may be suitable for implantation, e.g., in breast or prostate tissue. As illustrated in FIGS. 9-10, a planar device 130 includes a radioactive material 132 in a planar sealed casing 134. The radioactive material 132 may include one or more of the microcapsules 50, 60, 70. The sealed casing 134 may include two planar members 134A and 134B with the radioactive material 132 positioned therebetween.

Any suitable bioabsorbable or biodegradable material may be used, such as copolymers and homopolymers of glycolic acid (GA) and L-lactic acid (LA) or combinations thereof, including copolymers having a blend of these two base materials (e.g., Vicyrl (Polyglactin 910), for instance, is formed with a 90:10 GA-to-LA blend). Another example is a mixture of 18:82 GA-to-LA blend to achieve longer-term stability in the body. Atrisorb® (Zila, Inc., Fort Collins, Colo., USA), Resolut® (W.L. Gore and Associates, Inc., Neward, Del., USA), or Lactosorb® (Biomet Microfixation, Jacksonville, Fla., USA) may also be used.

In some embodiments, palladium-103 may be used in the radioactive microspheres 54 of the microcapsules 50 and 70; however, any suitable radioactive material may be used, including palladium-103, iodine-125, cesium-131 and phosphorus-32. Although palladium-103 and its daughter isotope rhodium are both in their elemental forms harmless, both palladium chloride and rhodium trichloride are toxic with intravenous rat LD50s of 3 mg/kg and 215 mg/kg respectively. Typically, palladium-103 is supplied in the chloride form. Thus, a bioabsorbable device that liberates the radio-isotope directly into the patient would likely face significant regulatory hurdles to ensure its long term safety. According to some embodiments, the outer surface of the microspheres is made of a leak-tight biocompatible material, such as glass or acrylic that may reduce or prevent chemical contact with the patient after bioabsorption of the microcapsule.

In particular embodiments, the flexible scaffold or support 20 of FIG. 1 has an outer diameter of about 0.8 mm and a length of up to 60 mm, and may be molded out of a flexible, bioabsorbable material, such as a poly-lactide/poly-glycolide co-polymer. These dimensions may be used so that the device may be applied with an 18 gauge brachytherapy needle. However, other suitable sizes may be used. Generally regularly spaced wells 22 in this support 20 contain radioactive and/or radio-opaque material. The radioactive material may be palladium-103, and the radio-opaque material could be a gold, iodine, or barium, including compounds and combinations thereof. Both the radioactive and radio-opaque materials are each contained within biocompatible microspheres as described herein.

The microspheres 54, 64 may have diameters between 1 and 20 microns. As illustrated in FIGS. 5-6, the microspheres 54, 64 may include a respective microsphere core 54A, 64A and an outer microsphere wall 54B, 64B. The outer microsphere walls 54B, 64B may be formed, e.g., of a leak-tight material such as glass or an acrylic, such as polymethylmethacrylate (PMMA). The radioactive core 54A may be formed of a radioactive material, such as palladium-103, alone or infused in a porous base (e.g., a porous polymer or glass material) or mixed with a polymer. The radio-opaque core 64A may be formed of any suitable radio-opaque material, such as gold, iodine or barium, including compounds and combinations thereof. Although the microspheres 54, 64 are illustrated in FIGS. 5-6 as having respective microsphere cores 54A, 64A and outer walls 54B, 64B, it should be understood that any suitable configuration may be used. For example, in some embodiments, the outer walls 54B, 64B are omitted and the microspheres may be formed of a generally homogeneous material, such as a radioactive material alone, infused in a porous base, or mixed with another material, such as a polymer.

To minimize the risk of aerosolizing the radioactive microspheres 54 or the radio-opaque microspheres 64 during manufacture, which may pose safety risks, these microspheres 54, 64 may in turn be contained in the bioabsorbable microcapsules 50, 60, 70, which may have a diameter of approximately 100 microns or more. These microcapsules may in turn be sealed into the wells 22 in the support 20 with a bioabsorbable material or well sealant.

The bioabsorption of devices according to some embodiments may proceed as follows. After three months (e.g., five half-lives of the palladium-103), a device using palladium-103 would have delivered 97% of the radiation dose. At that time, the bioabsorbable materials, e.g., including the scaffold support, the well sealant, and the microcapsule wall and other bioabsorbable materials, may begin to significantly decay in the patient's body. In some embodiments, the size and/or thickness of the scaffold support and other bioabsorbable materials may be selected so as to approximate a predetermined decay time, such as a decay time that is greater than two and a half times the half life of the radioactive material or five times or greater than the half life of the radioactive material. The decay process may liberate the microspheres 54, 64.

Without wishing to be bound by any particular theory, the size of these microspheres 54, 64 may be chosen so as to increase dispersement of the microspheres 54, 64 upon release. For example, macrophages in the patient's body may engulf the microspheres in the process of phagocytosis. Phagocytosis is the cellular process of engulfing solid particles by the cell membrane to form an internal phagosome by phagocytes and protists. In the immune system, phagocytosis is a mechanism used to remove pathogens and cell debris. Bacteria, dead tissue cells, and small mineral particles are all examples of objects that may be phagocytosed. For example, the microspheres 54, 64 may be about 1-20 microns, which may be a suitable size to be subject to phagocytosis. The microspheres 54, 64 may be sufficiently large so that the macrophages cannot transport the microspheres to the patient's lymph nodes where they may collect and appear confusingly similar to a cancer occurrence or recurrence with a CT or fluoroscopy scan. Instead, due to the size of the microsphere, the macrophages may disperse, but then fix in place, the microspheres 54, 64. The walls 54A, 64A of these microspheres 54, 64 may permanently contain both the decay products of the radioactive material core 54A and the radio-opaque material core 64A, respectively, for example, with a suitable material such as glass or acrylic, which may reduce or prevent direct contact with body tissue. As noted above, in some embodiments, the walls 54A, 64A may be omitted. Thus, the device may no longer be felt as a permanent implant by the patient and it may be appear to dissolve on a CT scan or other imaging scan because the radio-opaque markers in the microspheres 64 will have dispersed such that their visibility is reduced or eliminated. Exposure of healthy tissue to the potentially toxic components of the radioactive materials in the microspheres 54 may also be reduced or eliminated because sufficient radiation decay occurs prior to the release of the microspheres 54, 64 outside of the desired treatment area.

After a CT or MRI scan of the diseased tissue, such as a breast following a lumpectomy, health professionals, such as medical physicists in consultation with radiation oncologists, may plan the placement and location of the devices described herein so that a dose is delivered to the diseased tissue while sparing the adjacent healthy tissue. The number and lengths of the devices may be determined for the desired or optimal treatment plan, and therefore, devices according to some embodiments may be customizable for each patient. For example, for breast cancer, it is anticipated that between five to ten linear or string-shaped scaffold devices with lengths between about 1 and 6 cm may be needed to treat a malignancy. As in the case of seeds, the devices according to embodiments of the present invention may be applied in an outpatient setting with minimal anesthesia and the patient may likely leave the hospital the same day. A follow-up CT scan after implantation may be used to confirm device placement and perform quality control.

According to some embodiments of the present invention, a low-dose rate (LDR) brachytherapy device may reduce or minimize some of the practical problems with permanent seed implants with cancers such as breast cancer while maintaining the LDR technique's efficacy, lower side effect profile, and high convenience when compared to high dose brachytherapy or radiation beam treatment. In particular embodiments, a device of sufficient size to deliver a uniform or substantially uniform radiation dose and stay fixed in place in tissue, such as breast tissue, may have reduced dosimetry uncertainties than traditional seeds. Devices according to some embodiments may be made of flexible polymers and may be more comfortable for the patient than traditional seeds when implanted in soft tissue, such as breast tissue. A bioabsorbable device may reduce the concerns about subsequent mammograms, and cosmetic concerns about permanent implants in soft tissue, such as breast tissue. Moreover, devices according to the present invention may be customized for each individual patient.

In some embodiments, a bioabsorbable or biodegradable support or scaffold (such as the support 20 in FIG. 1, the casing 124 in FIG. 8, and the casing 134 in FIGS. 9-10) is fabricated from a bioabsorbable material such as a polylactide, poly-glycolide, polycaprolactone, poly-trimethylene-carbonate, polyanhdride, co-polymers formed thereof, combinations thereof, or any other suitable bioabsorbable or biodegradable material. The bioabsorbable material may be chosen so that it has a decay time in the human body that is long enough to allow sufficient decay of the radioisotope, e.g., longer than at least two half-lives of the radioisotope. The support can be formed by either injection molding, solvent casting, laser or mechanical machining or any other suitable method.

The microspheres containing a therapeutic radioisotope can be fabricated in a variety of ways. In some embodiments, the radioisotope is mixed with a biocompatible polymer, such as PMMA. The mixture may be achieved by dissolving both the radioisotope and the polymer in an appropriate solvent, or may be achieved by mixing the radioisotope into the polymer when the polymer is heated into a molten state. The radioisotope/polymer mixture may then be fabricated into microspheres through a variety of techniques (see, e.g., U.S. Patent Publication No. 2012/0121510) including solvent evaporation (see, e.g., U.S. Pat. Nos. 5,407,609; 5,650,173 and 5,654,008), phase inversion (see U.S. Pat. No. 6,235,224), or spraying methods (see U.S. Pat. No. 5,667,806), or other suitable techniques.

In some embodiments, the radioisotope may be mixed with a biocompatible ceramic, such as Schott™ 8625 glass, available from Schott, North America, Inc., Elmsford, N.Y., U.S.A.), in the molten phase. The glass/radioisotope mixture may then be formed into microspheres through various techniques including spraying methods (see U.S. Pat. No. 3,279,905). The biocompatible polymer or biocompatible ceramic microspheres may be further processed to the appropriate size, e.g., through a mechanical milling action (see U.S. Pat. No. 5,011,677).

In some embodiments, the microspheres may include three components: a porous inner core, the radioisotope, and a biocompatible shell. The porous inner core may be made of a porous polymer, such as polyethylene (see U.S. Pat. No. 3,865,674), a porous glass (see U.S. Pat. No. 3,513,106) or other suitable porous material. The porous material may be mechanically milled to the appropriate size. The radioisotope may be deposited as a liquid into the porous cores through a precision deposition process (See U.S. Pat. No. 7,686,756). The radioisotope could be converted from a soluble form into an insoluble form by various techniques, including exposing the soluble form to a plasma, by chemical precipitation and/or by exposing the soluble form to heat. Methods and devices for forming non-soluble radioactive materials are disclosed in U.S. patent application Ser. No. 12/434,131, filed May 1, 2009 and published as U.S. Publication No. 2009/0275793 on Nov. 5, 2009, the disclosure of which is incorporated herein by reference in its entirety. Once converted to an insoluble form, the core and radioisotope may be encapsulated in a biocompatible material using a spray-drying process, interfacial polymerization process (see U.S. Pat. No. 5,277,979) a pan-coating process or any other suitable method.

The microspheres containing a radio-opaque material may be fabricated as described above with respect to the microspheres that contain a therapeutic radioisotope except that a radio-opaque material, such as a gold or barium containing compound, replaces the radioisotope.

The microcapsules containing the microspheres (which in turn contain a therapeutic radioisotope or a radio-opaque material) may be fabricated, for example, by mixing the microspheres with a bioabsorbable material, such as polylactide, poly-glycolide, polycaprolactone, poly-trimethylene-carbonate or co-polymers formed thereof with a suitable solvent that does not dissolve the material or shell wall of the microspheres. The bioabsorbable shell may have a decay time in the human body that is sufficiently long to encase the radioisotope during its therapeutically useful lifetime and to release the radioisotope after significant decay has occurred, e.g., longer than at least two half-lives of the therapeutic radioisotope or more. This mixture may then be formed into microcapsules of specific size through any of the methods discussed above.

In some embodiments, the microcapsules are suspended in an emulsion containing a bioabsorbable material dissolved in an appropriate solvent such as toluene or xylene. The emulsion is then deposited in appropriate wells or otherwise affixed or embedded in the bioabsorbable or biodegradable scaffold or support. An emulsion containing the radioactive microcapsules may be deposited in some wells, the emulsion containing the radio-opaque microcapsules may be deposited in other wells or the radioactive microcapsules and radio-opaque microcapsules may be combined in a single emulsion. The solvent may then be allowed to evaporate leaving the microcapsules secured into the scaffold. Alternatively, the microcapsules may be mixed into a bioabsorbable or biodegradable material that is heated into a liquid state. In this heated state, the mixture containing radioactive microcapsules may be deposited in some wells, and the mixture containing radio-opaque microcapsules would be deposited in other wells, or a single mixture including both radioactive and radio-opaque microcapsules may be deposited. The heated mixture may be allowed to cool, thereby securing the microcapsules into the scaffold or support.

Although embodiments according to the present invention have been discussed with respect to breast and lung cancer, it should be understood that other tumor types may also benefit from a bioabsorbable brachytherapy device. It should be understood that other types of cancer may be treated using the methods and devices described herein, including bladder cancer, colon cancer, kidney or renal cancer, pancreatic cancer, prostate cancer thyroid cancer, head and neck cancers and soft tissue sarcomas. Moreover, in some embodiments, shielding materials may be strategically placed in brachytherapy devices described herein to provide generally uni-directional radiation and to protect healthy tissue adjacent cancer tissue. Moreover, in some embodiments, chemotherapy drugs or other therapeutic agents may be incorporated into the brachytherapy device and delivered to the tissue, e.g., when a portion of the device is bioabsorbed by the body.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are That which is claimed is:

1. A brachytherapy method comprising:
   implanting a low-dose-rate (LDR) brachytherapy device in a treatment region of a subject, the brachytherapy device comprising: a bioabsorbable support; and a plurality of microcapsules on the support, each of the plurality of microcapsules comprising a plurality of microspheres and a bioabsorbable microcapsule wall that encloses the plurality of microspheres, the plurality of microspheres comprising radiation-emitting microspheres comprising a radioactive material and radio-opaque microspheres comprising a radio-opaque material, wherein the plurality of microspheres are sized and configured so as to be subject to phagocytosis by macrophages in the subject after bioabsorption of the bioabsorbable support and the bioabsorbable microcapsule wall; and
   after a time sufficient for the support and microcapsule wall to bioabsorb in the subject and for phagocytosis to occur, imaging the treatment region of the subject to confirm that the radio-opaque microspheres are dispersed.

2. The method of claim 1, wherein the radio-opaque microspheres are dispersed by phagocytosis after bioabsorption in the subject.

3. The method of claim 1, wherein the plurality of radio-opaque microspheres have a diameter of about 1 to 20 microns.

4. The method of claim 3, wherein the plurality of radiation-emitting microspheres are dispersed by phagocytosis by macrophages in the subject after bioabsorption of the bioabsorbable support and the bioabsorbable microcapsule wall.

5. The method of claim 4, wherein the bioabsorbable support and the microcapsule wall have a decay time that is greater than about two and a half times a half life of the radioactive material.

6. The method of claim 1, wherein the radiation-emitting microspheres comprise a radioactive core and an outer wall.

7. The method of claim 6, wherein the radioactive core comprises a radioactive material and a biocompatible polymer and/or ceramic.

8. The method of claim 6, wherein the outer wall comprises glass or acrylic.

9. The method of claim 1, wherein the radiation-emitting microspheres comprise a porous material and a radio-isotope deposited therein.

10. The method of claim 1, wherein the microcapsule wall comprises a poly-lactide, poly-glycolide, polycaprolactone, poly-trimethylene-carbonate, polyanhydride, co-polymers formed thereof, and/or combinations thereof.

11. The method of claim 1, wherein the bioabsorbable support comprises a poly-lactide, poly-glycolide, polycaprolactone, poly-trimethylene-carbonate, polyanhydride, co-polymers formed thereof, and/or combinations thereof.

12. The method of claim 1, wherein the bioabsorbable support is configured to seal the microcapsules therein after implantation.

13. The method of claim 12, wherein a size and/or thickness of the bioabsorbable support and/or microcapsule walls is configured to release the microspheres after a predetermined time.

14. The method of claim 13, wherein the predetermined time is greater than two and a half times a half life of the radioactive material.

15. The method of claim 13, wherein the predetermined time is about three months.

16. The method of claim 1, wherein the bioabsorbable support comprises a seed casing that is configured to seal the plurality of microcapsules therein prior to bioabsorption of the support.

17. The method of claim 1, wherein the bioabsorbable support comprises a substantially linear support having a plurality of wells therein that is configured to seal the plurality of microcapsules in respective ones of the plurality of wells prior to bioabsorption of the support.

18. The method of claim 1, wherein the bioabsorbable support comprises a substantially planar support that is configured to seal the plurality of microcapsules therein prior to bioabsorption of the support.

* * * * *